United States Patent [19]

Laipply

[11] 4,427,111
[45] Jan. 24, 1984

[54] INTEGRAL ALCOHOL PREPARATION DEVICE AND METHOD

[76] Inventor: Thomas C. Laipply, 13530 Fox Den East, Russell, Ohio 44072

[21] Appl. No.: 312,880

[22] Filed: Oct. 19, 1981

[51] Int. Cl.³ .................. B65D 83/00; B65D 75/00; A61B 17/20
[52] U.S. Cl. .................... 206/210; 206/484; 206/812; 206/441
[58] Field of Search .............. 206/438, 441, 484, 530, 206/229, 812, 210; 15/104.93; 426/85, 125

[56] References Cited

U.S. PATENT DOCUMENTS

| | | | |
|---|---|---|---|
| 1,527,659 | 2/1925 | Wilkie | 206/530 |
| 1,810,453 | 6/1931 | Webster et al. | 426/85 |
| 2,760,630 | 8/1956 | Lakso | 206/530 |
| 3,035,300 | 5/1962 | Wattles | 206/229 |
| 3,240,326 | 3/1966 | Miller | 206/812 |
| 3,485,349 | 12/1969 | Chaney, Jr. | 15/104.93 |
| 3,580,254 | 5/1971 | Stuart | 206/441 |
| 3,635,567 | 1/1972 | Richardson, Jr. | 206/229 |
| 3,809,483 | 5/1972 | Young | 206/229 |
| 3,862,684 | 1/1975 | Schmitt | 206/438 |
| 3,903,345 | 9/1975 | Baker et al. | 206/484 |
| 3,986,640 | 10/1976 | Redmond | 222/92 |
| 4,053,053 | 10/1977 | Tumangday | 206/441 |
| 4,342,395 | 8/1982 | Brown | 206/530 |
| 4,372,098 | 2/1983 | Mason | 53/412 |

FOREIGN PATENT DOCUMENTS 644007  2/1964  Belgium .................. 206/820

OTHER PUBLICATIONS

Mason-Keller Corporation, Roseland, New Jersey 07068 USA, M-K Applicator Package, 4/24/78, U.S. Pat. No. 4,372,098.

*Primary Examiner*—William T. Dixson, Jr.
*Assistant Examiner*—Brenda J. Ehrhardt
*Attorney, Agent, or Firm*—Maky, Renner, Otto & Boisselle

[57] ABSTRACT

An integral alcohol preparation device or like type of fluid applying device includes an absorbent material or pad for containing alcohol or other fluid, a fluid impermeable material, for example of metal foil lined with plastic, as a selectively openable fluid tight chamber for the pad and fluid contained therein, and the pad and fluid impermeable material being attached as a substantially integral assembly. Being so attached, a method of using such a fluid applying device, then, may include the steps of manipulating the fluid impermeable material to open the chamber and to expose the pad and fluid contained therein without breaching the integrity of the several parts individually or collectively, and applying the fluid from the pad to an external surface. Further, a method is disclosed for making an integral fluid applying device. An alternate embodiment of fluid applying device includes a fluid permeable material and located therein a breakable fluid tight container containing the fluid.

25 Claims, 31 Drawing Figures

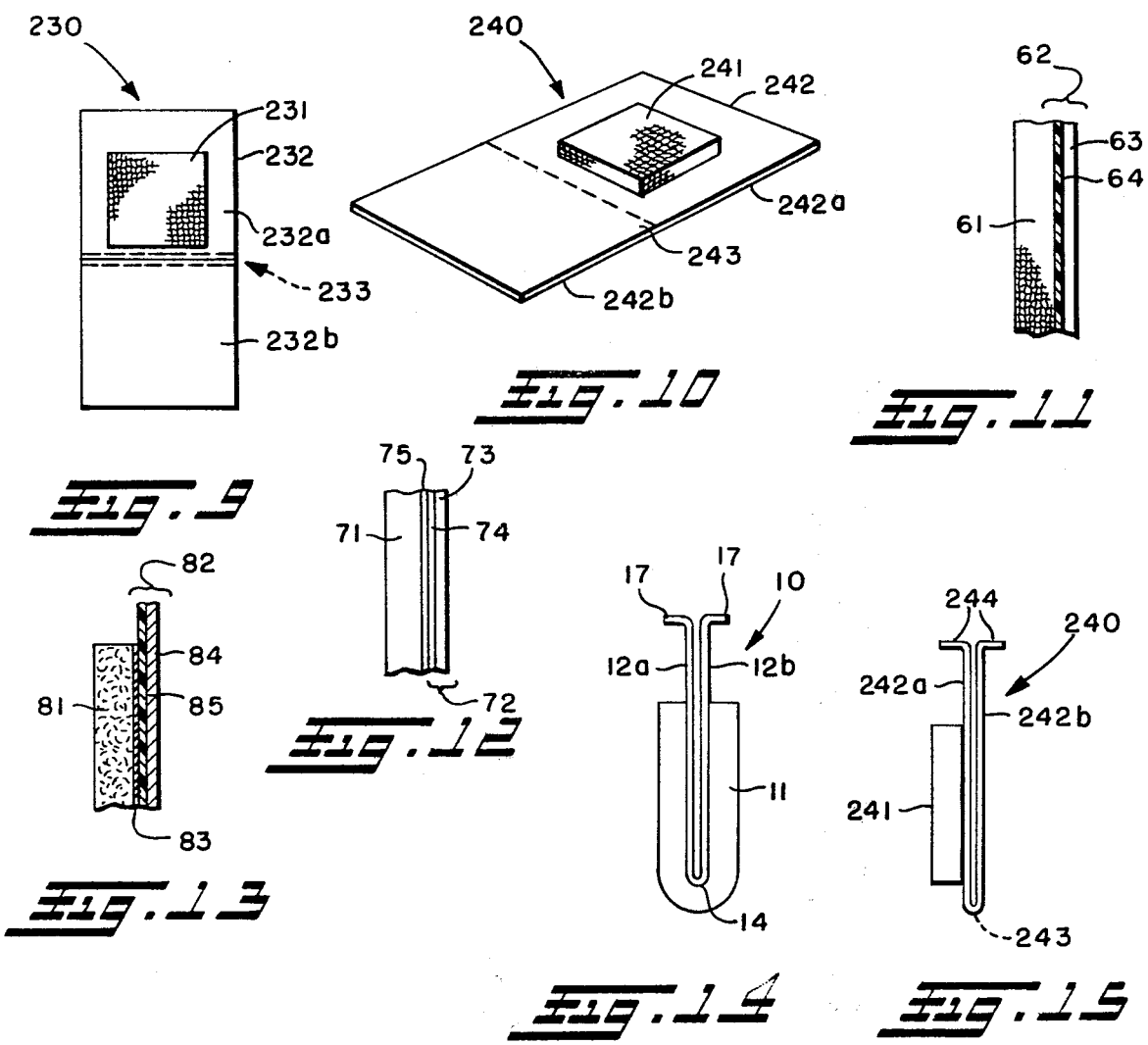

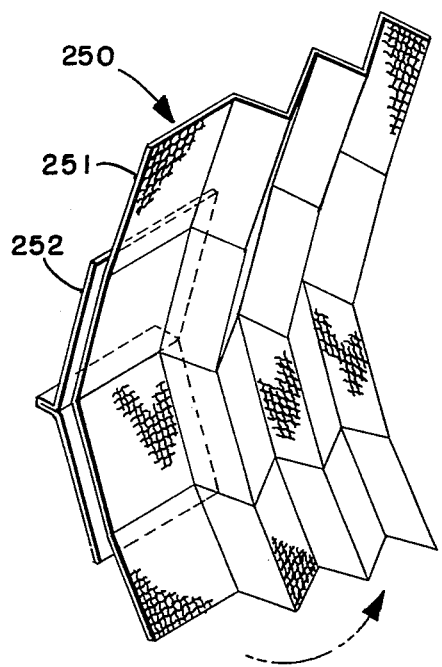
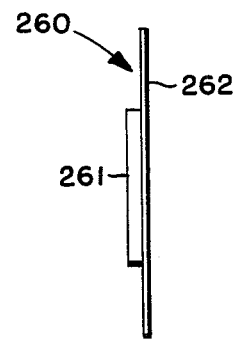
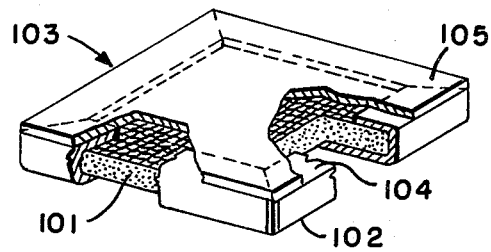
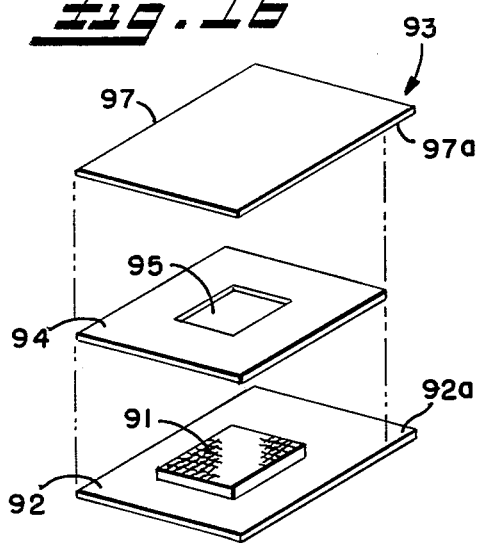
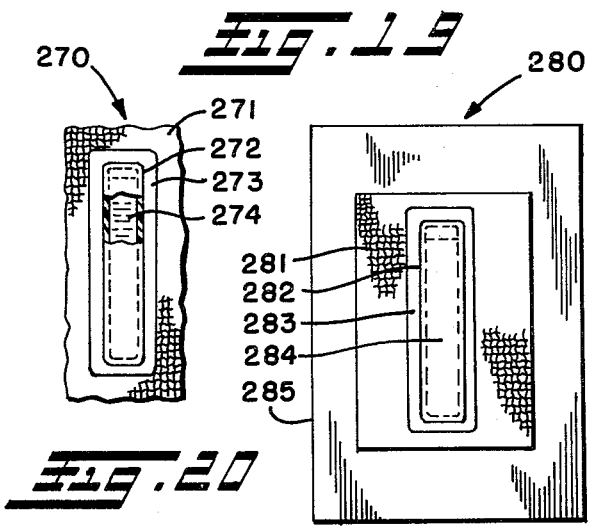
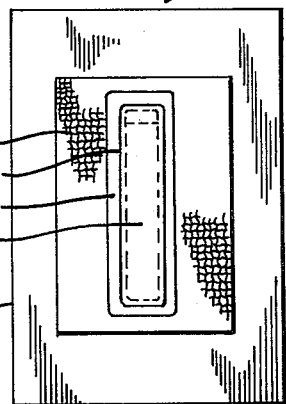
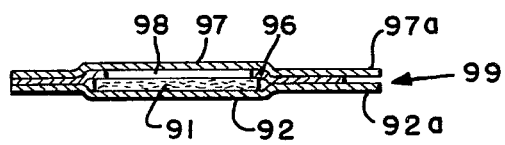

INTEGRAL ALCOHOL PREPARATION DEVICE AND METHOD

TECHNICAL FIELD

The present invention relates generally, as indicated, to fluid applying devices and methods and, more particularly, to such devices and methods in which a fluid permeable material containing a fluid is attached to a fluid impermeable material.

The invention will be described in detail below as relating to an alcohol preparation device, which is a device that contains alcohol or like fluid intended for sterilizing, cleaning or like purposes. However, it will be understood that the invention encompasses use of fluids other than alcohol or containing alcohol and other materials for sterilizing, cleaning or other purposes.

BACKGROUND OF PRIOR ART

Alcohol preparation devices have been known and used in the medical profession for a number of years. Such devices include alcohol absorbing material, such as a gauze or gauze like material which contains alcohol, and a fluid tight protective package that is sealed to define therein a chamber in which the absorbent alcohol containing material is contained. An example of one type of absorbent material is disclosed is U.S. Pat. No. 3,542,634; such material is used in the Webcol alcohol prep device sold by the Kendall Company, Boston, Mass., for example, for the purpose of applying sterilizing isopropal alcohol to the skin of a patient. Another example of such absorbent material and a package for containing the same is disclosed in U.S. Pat. No. 3,057,467; the absorbant material is a folded towlette containing a particular fluid for cleansing and refreshing a user and the package material is, for example, an aluminum foil with a thermoplastic liner. Such package material is impervious to the fluid contained therein, including both the liquid and vapor or gas forms thereof. Such material also is impervious to air and other materials that might otherwise contaminate the fluid and absorbent material contained in the package. The '467 patent discloses polyethylene, polyvinyl resin or cellulose acetate as suitable thermoplastic materials for providing a protective coating on the foil and for providing the impervious vapor-proof barrier desired; such materials also are readily heat sealable to seal closed the package. Other materials of which the package disclosed in the '467 patent may be made are celluloiic materials lined with a thermoplastic film or various synthetic or plastic materials. The device in the '467 patent is manufactured by forming a three part sandwich of two sheets of package material and the folded fluid impregnated towelette therebetween, and the edges of the package material sheets are heat sealed to each other about the entire permimeter of the package.

Several disadvantages inure to the prior fluid applying devices, such as the prior alcohol prep devices, towelette devices, etc. One disadvantage is that the package material must be torn to open the same in order to remove the absorbent material. Upon tearing of the package, the absorbent material may be torn, which may reduce usefulness thereof. Also, when the package is torn it may result in one and possibly two pieces and must be discarded, depending upon whether the tear fully severs one part from the other; and eventually the absorbent material also must be discarded separately. The separate discarding steps may waste time and may result in one or more pieces not reaching a proper waste container, e.g. a piece may drop on the floor and create a safety hazard. A further disadvantage particularly with respect to prior alcohol prep devices is that the user, such as a medical technician, nurse or physician, must physically touch surfaces of the absorbent material; this increases the potential hazard of contamination of the sterile condition of the absorbent material and frequent touching of that material often tends substantially to dry the skin of such user. Moreover, frequent flexing of the heat sealed package may result in loss of the seal integrity.

BRIEF SUMMARY OF THE INVENTION

With the foregoing in mind, the invention has an an objective overcoming of one or more of the above disadvantages of fluid applying devices, and especially those of the type known as alcohol preparation devices.

Accordingly, a primary object is to improve fluid applying devices.

Another object is to enable opening of an alcohol preparation device or the like without having to tear the package thereof.

An additional object is to enable opening of an alcohol preparation device or the like without producing multiple scraps.

A further object is to reduce exposure of a user of an alcohol preparation device or the like to fluid contained therein.

Still another object is to adhere flat absorbent material to the protective/impermeable material of an alcohol preparation device or the like.

Still an additional object is to improve the sterility of fluid applying material, e.g. of an alcohol preparation device or the like, especially during use thereof, and to improve the sterility of a fluid applying technique.

Still a further object is to improve the integrity of the seal of an alcohol preparation device or the like.

Yet another object is to improve the fluid tight integrity of an alcohol preparation device or the like.

Yet an additional object is to facilitate manufacturing of alcohol preparation devices or the like.

Yet a further object is to minimize the material required for an alcohol preparation device or the like.

Even another object is to minimize the cost of an alcohol preparation device or the like.

Even an additional object is to facilitate opening an alcohol preparation device or the like.

Even a further object is to provide an improved technique for use of an alcohol preparation device or the like.

Moreover, another object is to attach impermeable and absorbent materials of a fluid applying device as a functionally unified or one piece device.

Moreover, an additional object is to facilitate and to expedite sterilizing procedures.

Moreover, a further object is to avoid separate throw away pieces from a portable fluid applicator.

Yet even another object is to avoid tearing absorbent material of a fluid applying device.

Yet even an additional object is to provide a single piece device for storage and application of a fluid.

Yet even a further object is to permit use of a single piece fluid applicator without disrupting physical integrity of the device.

These and other objects and advantages of the invention will become more apparent as the following description proceeds.

In accordance with one aspect of the invention, a fluid applying device includes a containment means for containing fluid, a fluid impermeable means for forming a selectively openable fluid tight chamber for fluid of the containment means and an attaching means for attaching together the containment means and the fluid impermeable means as a substantially integral assembly.

According to another aspect there is provided in a fluid applying device including a fluid containment means for containing a fluid for application to an external surface or the like and a fluid imperemeable means sealed to form a fluid tight chamber for fluid contained in the containment means, the improvement comprising attachment means for attaching the fluid containment means and the fluid impermeable means as a substantially integral device.

According to an additional aspect, there is provided in a fluid applying device including a fluid containment means for containing a fluid for application to an external surface or the like and a fluid impermeable means sealed to form a fluid tight chamber for fluid contained in the containment means, the improvement comprising opening means for facile opening of the chamber to expose fluid without producing separate pieces from the device.

According to a further aspect, there is provided in a flow applying device including a fluid containment means for containing a fluid for application to an external surface or the like, the improvement comprising a fluid impermeable means for forming a fluid tight chamber for fluid contained in the containment means, the fluid impermeable means having a fold therein to form opposite portions of a package for such containment means, the portions being sealed along adjacent overlapping edges, and the sealed edges and the fold providing fluid tight integrity for the chamber.

According to yet another aspect, a method of using a fluid applying device in which containment means for containing fluid material is attached to a fluid impermeable means that is sealed to form a fluid tight chamber for such fluid contained by the containment means comprises manipulating the fluid impermeable means to open the chamber and to expose the containment means and applying such fluid from the containment means.

According to yet another additional aspect, a method of making a fluid applying device comprises attaching a fluid containment means and a fluid permeable material and sealing the fluid impermeable material to retain the fluid containment means therein.

According to yet a further aspect, a device for applying fluid to an external surface comprises fluid impermeable material and a breakable fluid tight container means for containing the fluid and positioned with respect to the fluid permeable material to deliver fluid thereto when broken without discharging physical parts of the container means through the fluid permeable material.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 9 is a plan view of an alternate integral fluid applying device in the open condition and in which the fluid containment material is only one-half of the fluid impermeable/package material;

FIG. 10 is an isometric view of an integral fluid applying device similar to that shown in FIG. 9 but in which one-half of the fluid impermeable/package material is intended to folded back or torn off relative to the other portion to which the fluid containing material is attached;

FIG. 11 is an enlarged fragmentary section view of a direct connection mechanism for an integral fluid applying device in accordance with the invention;

FIGS. 12 and 13 are enlarged fragmentary section views of additional attachment mechanisms for attaching the fluid containment material to the fluid impermeable/package material in accordance with the invention;

FIGS. 14 and 15 are schematic plan views of respective integral fluid applying devices showing a manner of use in which the two portions of fluid impermeable/package material are reverse folded;

FIG. 16 is an isometric view of a towelette type of integral fluid applying device;

FIGS. 17A and 17B are side elevation and section views, respectively, of a two part integral fluid applying device shown in open and closed conditions, respectively;

FIGS. 18A and 18B are, respectively, exploded isometric and side section views of a sandwich construction of integral fluid applying device employing a frame holder for holding the fluid containment material to the fluid impermeable/package material;

FIG. 19 is an isometric view, partly broken away in section, of a folded over frame/sandwich construction of integral fluid applying device;

FIG. 20 is a fragmentary plan view, partly broken away in section, of an alternate type of integral fluid applying device having a breakable vessicle within fluid permeable material; and FIG. 21 is a plan view of an integral fluid applying device of the type shown in FIG. 20 contained within a protective package.

BRIEF DESCRIPTION OF PRIOR ART FLUID APPLYING DEVICES

Figure 1A:
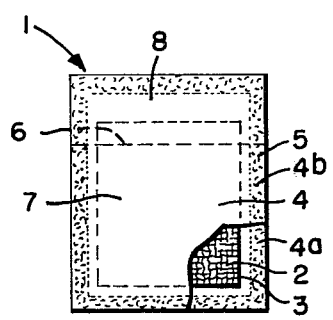
FIGS. 1A and 1B are plan views of a prior art fluid applying device of the alcohol preparation type or alcohol wipe type.
Figure 1B:
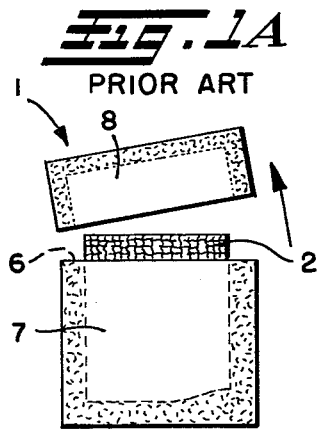

Referring briefly to FIGS. 1A and 1B, a prior art alcohol preparation device or alcohol wipe of the type mentioned above with reference to the Webcol device and the '634 and '467 patents is shown at 1. The device 1 includes a pad 2 of absorbent material for containing alcohol, such as, for example, a 70% isopropyl alcohol liquid. The pad 2 is contained in a chamber 3 formed in a package 4. The package 4 typically is formed of a metal foil that is coated or lined with thermoplastic material, for example, as is disclosed in the '467 patent. The lining material faces the chamber 3 so as to provide a fluid impermeable barrier to prevent escape of the alcohol by leakage, evaporation, or the like. The metal foil also provides a fluid impermeable barrier not only for the alcohol but also to prevent contamination of the materials in the chamber 3 from outside the package 4. The foil also provides additional support strength for the device 1. The package 4 is formed of two sheets 4a 4b of such lined foil material, and the sheets are head and/or pressure sealed to each other at respectively adjacent overlapping edges thereof around the perimeter of the device 1. The seal is indicated at 5 in FIGS. 1A and 1B.

A dashed line 6 in FIG. 1A is the tear line separating the main body 7 of the package 4 and a tear strip portion 8 thereof. During use of the device 1 a user tears the same approximately along the tear line 6 to separate the tear strip 8 in the manner shown in FIG. 1B exposing the chamber 3 and the pad 2 therein. Usually the tear strip 8 is totally separated from the body 7 and is discarded. After the pad 2 has been removed from the body 7, the latter also is discarded and the pad may be grasped manually by a user to apply alcohol to the surface, for example, the skin of a patient. The pad 2 subsequently may be discarded.

DETAILED DESCRIPTION OF THE INVENTION

As distinguished from the intentionally separable parts of the prior art device 1, the integral fluid applying device in accordance with the present invention does not have intentionally separable parts and can in fact be stored and used without destroying the attached or structural integrity of the several parts.

Figures 2A, 2B:
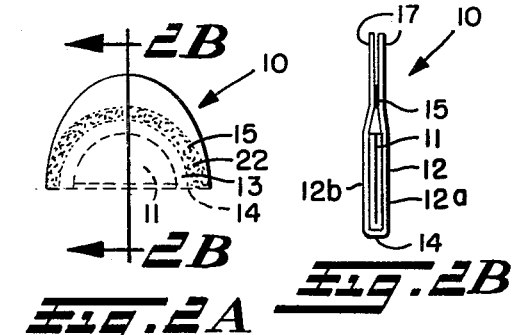
FIG. 2A is a plan view of an integral alcohol preparation device in accordance with the present invention in sealed or closed condition.
FIG. 2B is a section view of the alcohol preparation device looking generally in the direction of the arrows 2B—2B of FIG. 2A.
Figure 2C:
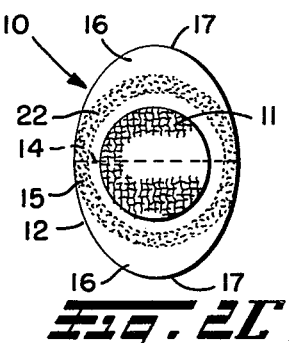
FIG. 2C is a plan view of the alcohol preparation device of FIG. 2A open and ready for use.

Referring now in detail to the drawings, wherein like reference numerals designate like parts in the several figures, and initially to FIGS. 2A through 2D, an integral fluid applying device in accordance with the preferred embodiment and best mode of the present invention is shown at 10. The device 10 includes a pad 11 attached to the fluid impermeable material 12, which may be closed in the manner shown in FIGS. 2A and 2B to form a fluid-tight chamber that may be opened in the manner shown in FIG. 2C to expose the pad 11 for use to apply fluid contained therein. The pad 11 is circular shape and the package 12 is oval shape, as is seen in FIG. 2C. Such shapes cooperate so that when the device 10 is folded (FIGS. 2A and 2B) along the fold line 14, the seal 15 may be a semi-circular anulus providing a minimum size for the chamber 13, on the one hand, while permitting the outlying portions 16 of the material 12 to form generally overlapping, but unsealed, tabs or flanges 17 which may be used to open the device 10 from its closed condition breaching the integrity of the seal 15.

The pad 11 may be formed of natural or synthetic material or a combination thereof. An example of the material of which the pad may be formed is conventional gauze material, material disclosed in the '634 patent, material of the type used in the Webcol device, foldable material of the type disclosed in the '467 patent, and the like. It is intended that the pad 11 be a fluid containment means, and, therefore, such pad preferrably is of a type of material that is absorbent of and permeable to the particular fluid it is intended to contain. Preferably such fluid is one containing alcohol, such as a 70% isopropyl alcohol mixture with water. Another fluid may be iodine, betadyne preparations, and other antiseptic solutions. Another example of a fluid that may be contained in the pad 11 is that disclosed in the '467 patent as a cleansing and refreshing agent. Other types of fluids also may be contained in the pad 11, such fluids most preferrably ordinarily taking a liquid form with the sealing of the chamber 13 preventing the loss by leakage or evaporation until the device 10 is intended for use.

The fluid may be applied to the pad 11 by soaking or by an injection technique. The dimensions of the pad 11 preferrably are smaller than those of the material of which the package 12 is formed to facilitate sealing of the package to form the chamber 13 and, additionally, to facilitate opening the package, for example by use of the flanges 17. The pad may be of fixed size or may be capable of unfolding (FIG. 16), and it may be on one side of the material of which the package 12 is formed, e.g. see FIGS. 9, 10, 15, 18A and 19, or it may be on both sides of the package, e.g. see FIGS. 2C, 3, 4, 7B, 8A, 8B, 14, 16, 17A and 17B. The material of which the pad 11 is formed should not be affected by the fluid it is intended to contain. Moreover, the pad 11 may be of a selected texture; for example, a rougher, more porous fibrous material may facilitate adhesion to the package material 12 and may provide some measure of abrasion when applying fluid to the skin of a patient, whereas a less textured material may retain larger quantities of fluid.

The material of which the package 12 is formed preferrably is a metal foil 20 (FIG. 2D), such as aluminum foil and a thermoplastic liner 21, such as a polyethylene material, a polyvinyl resin, or a cellulose acetate. Alternatively, the foil 20 may comprise a cellulosic material lined with a thermoplastic film or other synthetic or plastic materials. Such materials are of the type disclosed in the '467 patent.

The package material 12 should be relatively strong to resist unwanted penetration and it should be impermeable to ordinary external contaminants, such as air, dust, bacteria, etc., and impermeable to the fluid contained in the pad 11. Moreover, the material 12 should be unaffected by such fluid. The material 12 should be relatively flexible to permit ordinary manipulation and flexing that may occur during packaging, storage, and preparation for use, and it should be capable of being folded, for example, along the fold line 14, while maintaining the mechanical integrity of the material so that the zone in which the fold occurs remains as a fluid tight boundary for the chamber 13. The material 12 also should be attachable to the pad 11 by various means and techniques that will be described in greater detail below in order to form an integral device that during ordinary use is not intended to encounter separation of the pad 11 from the material 12. Further, the material 12 should be capable of being sealed at the seal zone 22 by thermal, mechanical, or other means. The material 12 should have adequate strength so that the force applied to the flanges or tabs 17 may be transmitted to the seal zone 22 in order to provide a relatively facile selective controlled opening of the device 10 while breaching the integrity of the seal 15 without damaging the integrity of other portions of the device 10.

The device 10 is oval in shape (FIG. 2C) and half-oval in shape when folded (FIG. 2A). The cooperative relation between the shape of the material 12 and that of the pad 11 is such that preferably the pad has smaller dimensions that the package material 12 to assure that the pad will be fully contained within the sealed chamber 13.

Figure 6A:
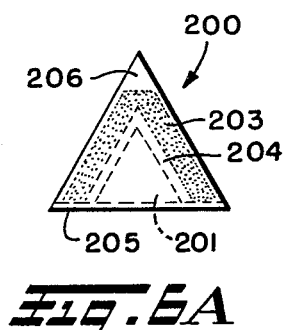
FIGS. 6A and 6B are plan views in the sealed and open conditions of a triangular/diamond integral fluid applying device.
Figure 6B:
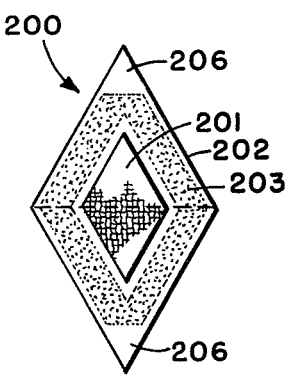
Figure 7A:
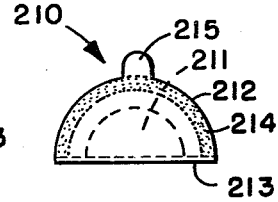
FIGS. 7A and 7B are plan views in the sealed and open conditions of a semi-circular/circular integral fluid applying device.
Figure 7B:
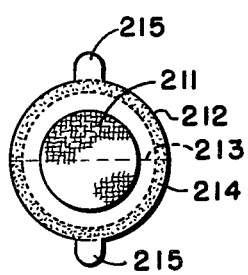

The oval shape or other curved shape, such as the circular form of FIG. 7A, 7B, is advantageous relative to a triangular/diamond shaped (FIGS. 6A, 6B) or rectangular shape (FIGS. 8A–8C) because there are no sharp corners protruding that possibly could cause an injury or discomfort to a user, to avoid the possibility of a sharp corner getting caught in a crevice such that removal therefrom would cause the device to open, and to minimize tearing of the package 12. The oval configuration provides the relatively large flanges 17 while requiring a relatively minimum quantity of material 12. The curved form, as well as the triangle/diamond form (FIGS. 6A, 6B) facilitate opening of the integral fluid applying device without tearing of the same by controlled application and a distribution of forces in a gradual and spreading manner to the seal zone 22; such forces also are applied such that more of the force is of a tensile type both at the outset of breaching the seal integrity and as the two portions 12a, 12b, for example, of the package 12 continue to be separated. In contrast, in a rectangular shape device the sheer component of force applied to the seal zone would be greater, would require greater force overall to open the device, and, additionally, would be more likely to effect a tearing of the material 12 itself. If desired, one of the flanges 17 may be longer than the other in order to facilitate separating them and opening of the device 10.

Seal 15 is a heat seal or pressure seal or a combination thereof. Specifically, it may be formed by applying heat in the seal zone 22 in order to cause a bonding of the thermoplastic liner 21 on opposite portions 12a, 12b of the package material 12. Pressure may be applied to assure good bonding characteristics in order to maintain a highly integral seal achieving substantially complete isolation of the chamber 13 from the environment external of the device 10. The seal may be formed in a variety of conventional manners, such as that disclosed in the '467 patent. If desired, crimping additional adhesive material, bonding material, or various liquid, semi-solid or solid materials may be applied at the seal zone 22 to respond to temperature, pressure, or other means for effecting a desired seal 15. Furthermore, the seal 15 preferably is capable of being broken to breach the integrity thereof when a force is applied to the tabs 17 in order to separate the portions 12a, 12b making the pad 11 accessible.

Preferably the seal 15 is formed between opposed portions 12a, 12b about the perifery or perimeter of the device 10 where there is no fold 14. However, the fold 14 completes the sealed integrity of the chamber 13. On the other hand, if the portions 12a, 12b were totally separate pieces, the seal provided by the fold 14 would be provided by the material and/or means similar to those described above with respect to the remainder of the seal 15. The material of which the seal is made should be unaffected by the fluid contained in the pad 11 and the seal should have adequate strength for relatively long term storage of the pad 11 without loss of the fluid from the chamber 13. The seal should be capable of being broken, as was noted earlier, with suitable force that will not damage the physical integrity of the remainder of the package material 12.

Figure 2D:
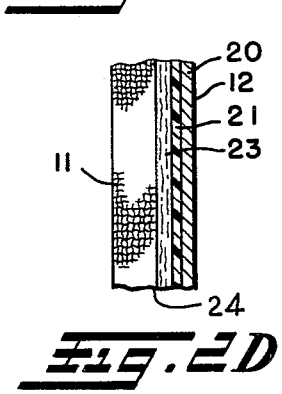
FIG. 2D is an enlarged fragmentary section view of a portion of the device of FIG. 2C.

Very importantly the pad 11 is attached to the package material 12. As is illustrated in FIG. 2D, such attachment is effected by an interface material 23 between the pad surface 24 and the plastic liner 21. The interface material 23 preferably is a material known as Parafilm sold by the American Can Company, Dixie/Marathon of Greenwich, Ct. Such interface material may be interposed between the pad 11 and plastic liner 21 and heat may be applied to one or both sides, for example, to the foil 20 and/or through the pad 11 causing the interface material 23 to tend to bond with the surface 24 and with the plastic liner 21. The shape of the interface 23 may be identical of the circular shape of the pad 11; alternatively the interface material may be larger or smaller in plan dimensions than the pad 11 or it may be in several pieces spaced at different places between the pad 11 and plastic liner 21, as may be desired to achieve the desired holding strength while minimizing the amount of interface material required for retention. The interface material 23 also should be unaffected by the fluid in the pad 11 and should be non-reactive chemically with any of the materials with which it comes in contact or proximity.

Other types of techniques may be used to attach the pad 11 to the package material 12. For example, glue (FIG. 4), tape, (FIG. 5) a direct heat seal (FIG. 11), an interposed plastic or plastic-like material (FIG. 12), a solvent (FIG. 13), or a frame-like cover (FIGS. 18A, 18B and 19) may be used for the purpose of holding the pad to the package material.

The pad may be attached to the package material either prior or subsequent to application of fluid to the pad; however, preferably the attachment is effected prior to delivery of the fluid to the pad. In particular, when a solvent or other curable adhesive, such as glue, is used to perform the attaching function, or when heat is necessary to effect attachment, it is desirable to permit solvents to evaporate or to permit the pad to cool before the fluid, such as alcohol, is applied to the pad. The interface material 23 also may be of a fluid impermeable type so as to cooperate further with the plastic liner 21 (or the liner 21 may be eliminated when a suitable interface material is used that will provide the fluid impermeability and suitable adherence to the foil or other material of which the outer layer of the package 12 is formed). Thus, the interface material 23 may enhance the interity of the seal 15. Moreover, the interface material 23 may be used to provide such seal function; for example, parafilm may be sealed in response to application of thermal energy in the same way that the plastic liner 21 (if used) may be sealed to maintain the fluid type integrity of the chamber 13. The strength of attachment of the pad 11 to the package material 12 should be adequate so that the two materials do not separate during ordinary usage of the device 10. The attachment of the pad 11 to the package material 12, then, should have suitable sheer strength due to the usual rubbing action that device 10 will undergo when applying fluid to a surface; whereas the tensile strength of the connection between the pad and package material is not quite as critical. The attaching material or technique also should be non-toxic for the device 10 often is used with humans, and, accordingly, the preferred Parafilm quite clearly is non-toxic. Other than Parafilm, other types of wax, saturated hydrocarbons, paraffin, or like materials also may be used for attaching the pad 11 to the package material 12. Such materials tend to provide an excellent bond, are unsticky when solidified, clearly are non-toxic, do not contain organic solvents, and would not hinder opening of the seal 15. Gelatin also may be used for attaching the pad to the package material; but gelatin ordinarily is more difficult to work with than the preferred wax material.

Summarizing, then, a device 10 in accordance with the present invention includes a means (the pad 11) for absorbing and containing fluid, a means (the package material 12) that provides an impermeable barrier to the fluid whild also permitting mechanical flexibility of the device, attachment of the foregoing means to make the device integral, and an externally applied, e.g. by force, heat, or the like, seal 15.

A device 10 in accordance with the present invention may be manufactured, for example by the following steps. The package material 12 is cut to the desired shape. For example, such package material may include foil already coated with a plastic liner. A fold or crimp may be applied (FIGS. 8A-8C) if a handle is to be provided on the device. The interface material 23 is placed into engagement with or applied to the package material, and then the pad 11 is applied by placing the same into engagement with the interface material. Heat is applied to cause the interface material to bond with the pad 11 and package material 12. (If the heat were to cause a disruption of the plastic liner 21, the interface material 23 may provide compensation therefor.) Alcohol or other fluid is applied to the pad 11, and the device then is folded, for example to the configuration shown in FIGS. 2A and 2B. The seal 15 is formed by applying heat and/or force to the perimeter of the device defining the area of the chamber 13 while preferably not bonding the flanges 17 together, which should remain separable for facile manual grasping and opening of the device 10.

To use the device 10, the same may be held by a user and manipulated to open the device exposing pad 11. More specifically, the flanges 17 may be grasped between the thumb and forefinger, for example, of both hands of the user and force tending to separate the flanges may be applied. Such force should be adequate to break the seal 15 allowing the device 10 to be opened along the semi-circular seal zone. When the device is fully open, whereupon the fold 14 is straightened so that the device is substantially flat in the manner shown in FIG. 2C, the user may grasp one of the flanges 17 between thumb and forefinger while using the fingers of the same hand against the package material 12 behind the area in which the pad 11 is located to provide a backing therefor; and the pad may be rubbed against a surface, such as the skin of a patient, to apply fluid from the pad to the surface, e.g. for sterilizing, cleansing or like purposes.

Figure 3:
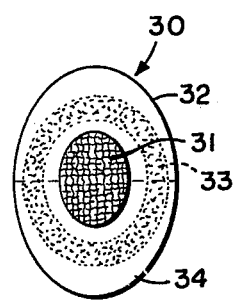
FIG. 3 is a plan view of an alternate integral fluid applying device shown open and ready for use.

Referring now to FIG. 3, a modified device 30 is shown there. The device 30 includes an oval shape pad 31 and oval shape package material 32, which are similar to the pad and package materials 11, 12 described above. The pad 31 and package material 32 may be secured together by the various techniques disclosed herein. An advantage to the configurational device 30 is that the oval pad 31 may have a larger surface area exposure relative to the size of the package material 32 than does the circular pad 11 of FIG. 2C, for example. However, a disadvantage to the device 30 relative to the device 10 is that the seal zone 33 will take on a half-oval shape that reduces the effective free area of the respective tabs 34, thus reducing the exposed area thereof available to be grasped by a user to open the device 30. Although the device 30 is shown in its open position, it will be appreciated that such device may be folded over and sealed in the manner described above with reference to the device 10.

Figure 4:
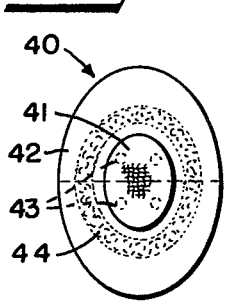
FIG. 4 is a plan view of another alternate fluid applying device open and ready for use, such device employing an alternate form of attachment means.

Turning now to FIG. 4, the integral fluid applying device 40 includes an oval pad 41 attached to oval package material 42 of the types described above with reference to the device 10. However in the device 40 glue 43 or like adhesive is used to effect attachment of the pad 41 to the liner, for example, of the package material 42. The device 40 is shown in open condition, although the seal zone 44 is shown, and such zone ordinarily would provide a complete seal for the device 40 in the manner described above with reference to the seal 15.

Various types of solvent or solvent base materials may be used for the glue or adhesive 43. Preferably the fluid intended to be applied to the pad 41 is not applied thereto until such solvents would evaporate. A preferred adhesive, which has been found ordinarily to be non-toxic and highly effective, is Ross Rubber Cement sold by Ross Chemical Co., Detroit, Mich. The various glues 43 may be applied by dabbing, rollers, swabbing, spraying, and the like.

Figure 5:
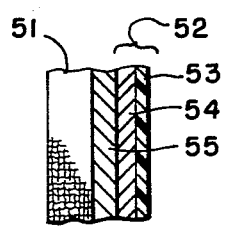
FIG. 5 is an enlarged fragmentary view of an integral fluid applying device using another form of attachment means.

In FIG. 5 is a fragmentary view of a technique for attaching a pad 51 to a package material 52, which includes a foil material 53 and a thermoplastic liner 54. Such technique employs tape 55 which may be a type of tape having adhesive material on both the sides thereof.

Jumping to FIG. 11, another attachment technique for attaching a pad 61 to package material 62 of an integral fluid applying device is illustrated. Such package material 62 includes, for example, a foil material 63 and a thermoplastic liner 64. Such thermoplastic liner 64 preferably has suitable thickness and is adequately responsive to applcation of thermal energy thereto in order to maintain the fluid tight integrity of the chamber formed in the fluid applying device, such as the chamber 13 described above, while also in response to the applied thermal energy forming a bond with the pad 61. It is noted here that since the bond ordinarily should be relatively strong to shear forces, the small degree of melting of the plastic liner 64 and interfacing of the surface thereof with a relatively rough surface of the pad 61 will provide a good measure of shear force retention. On the other hand, although the penetration of the plastic material of the liner 64 ordinarily would not be very deep into the pad 61, the same is not essential since it usually will not be necessary for the bond therebetween to be resistive to high levels of tensile force.

The fragmentary view of FIG. 12 is another example of a technique for attaching a pad 71 to package material 72, which includes a foil 73 and a thermoplastic material 74, for example. Such technique employs the use of a plastic interface material 75, such as plastic wrap, for example the type sold under the trademark Saran.

In FIG. 13 the pad 81 is attached to the package material 82 by a solvent represented at 83. The package material 82 again may be of a foil 84 having a plastic liner 85. The solvent 83 preferably affects both that portion of the pad 81 and that portion of the liner 85 with which it comes in contact so as to effect a bond between those respective portions. A synthetic sponge would be an example of a suitable solvent responsive material as the pad 81.

Various techniques described above for attaching a fluid absorbant pad, such as pad 11 to fluid impermeable material, such as the package material 12 of the device 10, may be employed in the various embodiments of the integral fluid applying devices of the invention disclosed herein and equivalents thereof.

Briefly referring to devices 90, 100 in FIGS. 18A, 18B and 19, respective sandwich type fastening techniques for securing respective pads 91, 101 to package material sheets 92, 102 are illustrated. In the integral fluid applying device 93 of FIGS. 18A and 18B, a picture frame type of sheet 94 of rectangular angular configuration having a central opening 95 is secured to the sheet 92, which may be of foil having a plastic liner, such that perimeter edges of the anulus adjacent the opening 95, for example as is shown at 96, overlap a portion of the pad 91 to hold the same in engagement with the package material sheet 92. A cover sheet 97, also, for example, of foil with an inner plastic liner is attached to the sheet 94 to close an internal chamber 98. Various seal techniques may be used for the device 93 to maintain the fluid tight integrity of the chamber 98. For example, the several sheets 92, 94 and 97 may be sealed about the perimeter 99 using thermal sealing techniques, pressure sealing techniques, or the like. Also, if desired, flanges 92a, 97a or other means to facilitate removal of the sheet 97 from the combination of pad 91, sheet 92 and frame 94 may be provided either to permit full removal of the sheet 97 or, alternatively, partial removal thereof while still remaining attached to the remainder of the device 93 as the pad 91 still is exposed for use.

In the integral fluid applying device 103 of FIG. 19 the edges 104 of the sheet 102 are folded up and over the pad 101 to retain the same within a frame-like holder formed by the package material 102, which may be foil lined with a plastic liner, as was described above. A cover sheet 105 may be sealed in position shown in FIG. 19 using the various seal techniques described above. Also, the cover sheet 105 may be removed from the sheet 102 by using a flange (not shown) that may facilitate grasping of the sheet 105 to peel the same partly or wholly off the sheet 102.

The fastening, enclosing and sealing techniques disclosed in FIGS. 18A, 18B and 19 also may be utilized in the various other embodiments of the invention, as may be desired.

Referring back to FIGS. 6A and 6B, a triangle/diamond shape integral fluid applying device 200 is illustrated. Such device includes a diamond shape pad 201 and a diamond shape package material 202, for example of the type described above with reference to the pad and package material 11, 12. The seal zone 203 also is illustrated, and when the device 200 is in closed condition the fluid-type chamber 204 is provided by the seal 203 and fold 205. In the closed condition of the device 200 pointed tabs 206 are conveniently available for separation and grasping by a user to facilitate opening the device to use the same in the manner described above.

A circular/semi-circular integral fluid applying device to 10 is illustrated in FIGS. 7A and 7B in which the pad 211 and package material 212, for example of the type described above with reference to FIGS. 2A–2D are of generally circular shape and fold along the fold line 213 to semi-circular shape. The seal zone 214 also is of anular circular or sem-circular shape, as is illustrated. Moreover, tabs 215 in the package material 212 may be grasped manually by a user to facilitate opening the device from the closed condition shown in FIG. 7A to the open condition of FIG. 7B for use.

Figure 8A:
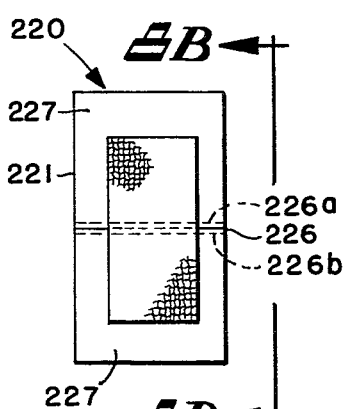
FIGS. 8A, 8B and 8C are open plan, side elevation and closed plan views of a rectangular integral fluid applying device with a user grasp tab or handle.
Figure 8B:
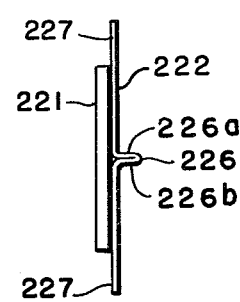
Figure 8C:
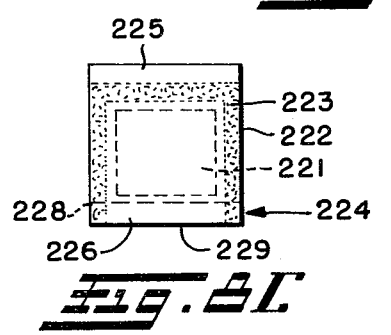

A rectangular integral fluid applying device 220 in FIGS. 8A, 8B and 8C includes a rectangular pad 211 of the same shape as the package material 222 of the type described above, for example with reference to FIGS. 2A–2D. The seal zone 223 for the device 220 extends in generally rectangular angular manner from the area 224 which ordinarily would be the fold line, for example at 14 in FIG. 2D, leaving available unsealed flanges 225 which may be grasped to open the device 220. Importantly, the device 220 includes a user grasp tab or handle portion 226. Such handle portion 226 is formed by folding or crimping the package material 222 in the manner shown in FIG. 2B prior to attaching the pad 221 to the surface 227. The two sides 226A, 226B of the package material which form the handle 226 may be heat sealed together so that the junction 228 is in effect one side of the seal zone 223. Alternatively, the seal zone 223 may extend in the manner shown in FIG. 8C into the handle 226 so that the boundary 229 of the handle at which there is a clear fold, analogous to the fold 14 of the device 10, provides a closing side or leg of the seal for the internal chamber of the device 220.

In using the device 220 a user may grasp the flanges 225 and may apply a force to open the seal 223 exposing the pad 221 without actually touching the same or any fluid contained therein. With the device 220 open to the condition shown in FIGS. 8A and 8B, then, the user may grasp the handle 226 and use the latter to rub the device 220 and particularly the pad 221 against a surface to which fluid is be applied, for example, the skin of a patient. After such use, the device 220 may be discarded. The handle 226 may be employed as part of the several integral fluid applying devices disclosed herein especially to facilitate use without the user having to touch the fluid contained in the pad.

In FIG. 9 an integral fluid applying device 230 is substantially identical to the device 220 except that the pad 231 extends only on one-half portion of the package material 232, particularly that portion identified as 232a. The portion 232b of the package material is used primarily for a cover. The seal zone in the device 230 is not shown, but it would be, for example, of the type shown in FIG. 8C. Moreover, the dashed lines approximately across the middle of the device 230 represent a handle 233 for the device 230 of the type shown at 226 in FIG. 8B.

An integral fluid applying device 240 illustrated in FIG. 10 also includes a pad 241 attached only one one-half portion 242a of the package material 242. The other half 242b of the package material may provide simply a cover for the pad and, if desired, may be removed by tearing the same along the tear line 243 if desired. Alternatively, the portion 242b may be folded back or reverse folded to remove any non-sterile surface from exposure to the pad 241 in the manner shown in FIG. 15. When so folded back in the manner shown in FIG. 15, the portions 242a, 242b are positioned back to back or foil to foil and the flanges 244 are positioned as shown in such figure. The device may be grasped by a user, then, and used to apply fluid to a surface.

In addition to the reverse folded form for use of the device 240 in the manner shown in FIG. 15, various other devices, such as devices 10, 30, 40, 200, 210, and the like, may be used in the reverse folded form of FIG. 14. Thus, for example, the device 10 used in the reverse folded form of FIG. 14 would have the flanges 17 near the top, the package material portions 12a, 12b back to back, and the pad 11 fully exposed for wiping against a surface. The user, such as a technician, need not touch that pad portion which is intended to be placed in engagement with the skin of a patient, for example, in either usage technique of FIGS. 14 or 15.

An integral fluid applying device 250 in FIG. 16 includes a towelette 251 attached to package material 252. The package material 252 may be of the type described above. The towelette 251 is formed of absorbent material, such as that disclosed in the '467 patent. The towelette 251 may be folded to a relatively small size to fit within a chamber formed by a sealed package 252. The towelette 251 contains, for example, a cleaning and refreshing fluid, such as that disclosed in the '467 patent, or other fluid material, as may be desired. When the seal on the device 250 is broken and the device is opened, the towelette 251 may be unfolded in the manner shown in FIG. 16 for use to wipe a surface, such as the skin of a person.

It is noted here that although the towelette 251 and the other absorbent materials disclosed herein are most preferably intended ordinarily to contain a fluid to be applied to another surface, for example, when the device is opened, equivalently such absorbent materials may be employed for the purpose of wiping or absorbing materials from an external surface. In such case, the package, such as the package 252 of the device 250, or any of the other packages disclosed herein, may be used for the purpose of maintaining the absorbent material clean or sterile.

Choice of the preferred plastic lined foil material, such as that described above as material 12 in the preferred embodiment of FIGS. 2A-2D, currently is founded on the fact that such material ordinarily is used in conventional alcohol preparation devices, such as the Webcol device mentioned above, is available commercially, and is known to be satisfactory for conventional alcohol preparation and towelette devices. However, the package material may be of other types, as also was mentioned above. An example of another type of package material may be simply a plastic or plastic type of material to which the absorbent material may be directly, e.g. as was described above with reference to FIG. 11, or indirectly, e.g. as was described in connection with FIGS. 2A-2D, connected; a foil; cellulosic materials; and/or various combinations thereof.

Another form of package material may be a wax or paraffin type of material, and this case is illustrated in the device 260 of FIGS. 17A and 17B. In the device 260 the pad 261 is formed of absorbent material of the type described above, such as with respect to the pad 11 of FIGS. 2A-2D, but the package material 262 is the above mentioned wax, paraffin or like material, and most preferably the aforementioned Parafilm. Such Parafilm is adequately flexible so that it can be folded at 263 to form a chamber 264 that is sealed about the remaining perimeter of the folded device 260 of FIG. 17B at the seal 265. Flanges 266 are available to be held by a user for applying pressure to breach the seal integrity opening the device 260 to the form illustrated in FIG. 17A for use in the various manners described above.

Alternate forms of the invention are shown in FIGS. 20 and 21. In those embodiments there are devices 270, 280 which are comprised of fluid absorbent or permeable material 271, 281, respectively, and a breakable vessicle 272, 282 contained within respective chambers 273, 283 formed by the absorbent material. The vessicles 272, 282 contain liquid 274, 284 and ordinarily prevent loss, e.g. by leakage or evaporation, or contamination of such liquid during storage. A user may apply pressure to the respective devices 270, 280 in a manner such that the pressure is transferred to the respective vessicles 272, 282 to break the same allowing the liquid 274, 284 to permeate the material 271, 281 while the material itself confines or restricts the vessicle and any pieces thereof to the chamber 273, 283. The liquid in the material 271, 281, then, may be applied in a manner similar to that described above, for example by wiping the device 270, 280 on the skin of a patient, or the like. An example of a satisfactory vessicle 272, 282 may be a gelatin capsule type of structure that may crack upon application of pressure thereto but which will not produce multiple pieces upon cracking.

The device 270 may be contained in a box, dispenser, or other structure that will maintain the device 270 satisfactorily clean or sterile, as may be desired, prior to use thereof. On the other hand, the device 280 preferably is contained within an impermeable package 285. Such package 285 may be formed of metal foil, plastic lined metal foil, wax, paraffin, or the various other materials described above for use as package materials. The package material 285 may be opened in the manner disclosed in FIG. 1B, i.e. according to the prior art technique, or the package material 285 may be, and most preferably is, attached to the absorbent material 281 to form an integral device therewith and may be capable of opening in one of the manners described above that does not destroy the integrity of the connection between the absorbent material 281 and package material 285.

STATEMENT OF INDUSTRIAL APPLICATION

With the foregoing in mind, it will be appreciated that the integral fluid applying devices in accordance with the present invention may be used to maintain relatively clean or sterile conditions of a fluid applying device and to keep the fluid ready for use, e.g. preventing evaporation or leakage thereof. The fluid may be a cleasing, refreshing, sterilizing, or like fluid. The invention also relates to methods of making the integral fluid applying devices and of using the same for cleaning, refreshing, sterilizing or like fluid applying purposes.

What is claimed is:

1. A combined fluid storage and application device comprising a single integral sheet of fluid impermeable material folded in generally symmetrical halves over on itself along a fold line positioning said halves in generally flat parallel overlying relation to each other, temporary seal means sealing said halves to each other along a temporary seal line which begins and ends at the fold line, a fluid retaining cavity having substantially flat parallel opposed wall surfaces formed by said halves, said fold line and said temporary seal line cooperating to define the periphery of said fluid retaining cavity, a fluid retaining pad disposed in said cavity and adhered to said sheet, and separation means for simultaneously applying separating force substantially symmetrically to both said halves of said sheet and to said temporary seal line without tearing said sheet, said separation means including means for applying simultaneously continuous separating force in multiple directions to open said sheet from folded condition fully exposing said cavity and said pad while the integrity of said sheet is maintained.

2. A device as set forth in claim 1 wherein said temporary seal line is spaced inward from the periphery of said sheet of material.

3. A device as set forth in claim 2 wherein said temporary seal line is a continuous curve.

4. A device as set forth in claim 2 wherein said temporary seal line consists essentially of straight lines.

5. The device of claim 4 wherein said pad is diamond shaped.

6. The device of claim 1 said impermeable material comprising plastic.

7. The device of claim 1 said impermeable material comprising paraffin.

8. The device of claim 1 wherein said temporary seal line forms a semi-oval shape when said material is folded on itself and said pad is circular.

9. The device of claim 1 wherein said temporary seal line forms a semi-oval shape when said material is folded on itself and said pad is oval shaped.

10. The device of claim 1, said fluid retaining pad covers approximately one-half the surface of said material enclosed by said temporary seal line when said material is unfolded whereby the other half of said material enclosed by said temporary seal line comprises a cover for said cavity.

11. The device of claim 1, wherein said separation means includes means for facilitating applying force to said temporary seal means to breach the same and to open said chamber to expose said pad, said means for facilitating comprising protruding opposite unsealed portions of said halves of said sheet of impermeable material.

12. The device of claim 11, said impermeable material being of rectangular shape, and said fold line extends between diagonally opposite corners of said rectangle.

13. The device of claim 11, said impermeable material being of diamond shape when unfolded and open and of generally triangular shape when folded over on itself.

14. The device of claim 13, said protruding portions comprising a tab-like portion at one apex of each triangle.

15. The device of claim 3, wherein said separation means includes means for facilitating applying force to said temporary seal means to breach the same and to open said chamber comprising curved tab-like extensions of said impermeable material.

16. The device of claim 15, said impermeable material being of oval shape when unsealed and open and of semi-oval shape when folded closed and sealed.

17. The device of claim 16, said temporary seal means enclosing a semi-circular seal zone between respective opposite faces of said folded impermeable material whereby unsealed extensions of the folded oval halves form said means for facilitating.

18. The device of claim 17, said pad being of circular shape when open and of semi-circular shape when folded in said chamber, and wherein said temporary seal line generally circumscribes a parallel curved path with respect to such folded semi-circular shape of said pad.

19. The device of claim 1, further comprising handle means for facilitating holding of such device for use.

20. The device of claim 19, said handle means comprising a crimp in said sheet of impermeable material.

21. The device of claim 19, said handle means comprising approximately a 180° reverse fold in said sheet of impermeable material out of the major plane of said sheet material.

22. The device of claim 21, said pad comprising material absorbent and permeable to such fluid and attached to said material in the plane thereof while covering the junction of said handle means with the major planar extent of said sheet of material.

23. The device of claim 22, said temporary seal means comprising a thermally created seal, and said impermeable material comprising foil with a thermoplastic liner and said temporary seal means comprising a seal of respective portion of said liner.

24. The device of claim 4, wherein said temporary seal line consists essentially of two straight lines which intersect at an acute angle.

25. The device of claim 1, wherein said separation means comprises means for applying such separating force initially at the approximate midpoint of said temporary seal line to cause such separation to proceed at least substantially equally in two directions from said approximate midpoint of said temporary seal line to said fold line.

* * * * *